(12) United States Patent
Aflatoon et al.

(10) Patent No.: US 8,986,305 B2
(45) Date of Patent: Mar. 24, 2015

(54) METHOD OF LATERAL FACET APPROACH, DECOMPRESSION AND FUSION USING SCREWS AND STAPLES AS WELL AS ARTHROPLASTY

(76) Inventors: Kamran Aflatoon, Corona del Mar, CA (US); Chris Maurer, Wakefield, MA (US)

( * ) Notice: Subject to any disclaimer, the term of this patent is extended or adjusted under 35 U.S.C. 154(b) by 597 days.

(21) Appl. No.: 12/836,879

(22) Filed: Jul. 15, 2010

(65) Prior Publication Data
US 2010/0280555 A1    Nov. 4, 2010

Related U.S. Application Data

(63) Continuation-in-part of application No. 12/283,438, filed on Sep. 11, 2008, now Pat. No. 8,894,651.

(60) Provisional application No. 60/993,233, filed on Sep. 11, 2007.

(51) Int. Cl.
| | |
|---|---|
| *A61B 17/064* | (2006.01) |
| *A61B 17/88* | (2006.01) |
| *A61B 17/90* | (2006.01) |
| *A61B 17/84* | (2006.01) |
| *A61B 17/34* | (2006.01) |
| *A61B 17/70* | (2006.01) |
| *A61F 2/44* | (2006.01) |
| *A61B 17/86* | (2006.01) |
| *A61B 17/02* | (2006.01) |
| *A61B 19/00* | (2006.01) |
| *A61F 2/30* | (2006.01) |

(52) U.S. Cl.
CPC ......... *A61B 17/3468* (2013.01); *A61B 17/0642* (2013.01); *A61B 17/3421* (2013.01); *A61B 17/7064* (2013.01); *A61B 17/8625* (2013.01); *A61B 17/864* (2013.01); *A61B 2017/0256* (2013.01); *A61B 2019/481* (2013.01); *A61F 2/4405* (2013.01); *A61F 2/4455* (2013.01); *A61F 2002/30576* (2013.01); *A61F 2002/30784* (2013.01); *A61F 2002/3085* (2013.01); *Y10S 606/914* (2013.01); *Y10S 606/915* (2013.01); *Y10S 606/916* (2013.01)
USPC ............ 606/75; 606/99; 606/86 A; 606/86 B; 606/914; 606/915; 606/916

(58) Field of Classification Search
USPC ............. 606/297, 75, 329, 99, 100, 104, 142, 606/86 A, 86 B, 914–916; 81/44, 440, 450, 81/456, 461; 403/311, 348–352; 285/331, 285/376, 396, 399, 401, 402
See application file for complete search history.

(56) References Cited

U.S. PATENT DOCUMENTS 4,793,335 A  * 12/1988  Frey et al. .................. 623/13.14
2004/0220569 A1* 11/2004  Wall et al. ...................... 606/61

*Primary Examiner* — Michael T Schaper
(74) *Attorney, Agent, or Firm* — Ober, Kaler, Grimes & Shriver; Royal W. Craig; Christopher F. Lonegro

(57) ABSTRACT

A method of performing vertebral facet fusion by lateral approach and related devices. The lateral approach to facet fusion involves identifying the lateral mass and introducing any of the fixation methods known or described herein laterally at one or more facets through the use of a Kirschner wire guide, a cannulated bone drill and cooperatively cannulated staple guide. A surgical bone staple have a perforated bridge is used across the lateral facet joint where fixation is required. Where fusion is desired, a bone screw have lateral perforations of the shank is inserted through the cannulated staple guide and bridge perforation at the joint to promote fusion. A staple cap and graft container for overlay grafting may be utilized for additional fusion. The method involves less surgical time, reduced blood loss and discomfort for the patient as compared to the posterior approach.

12 Claims, 12 Drawing Sheets

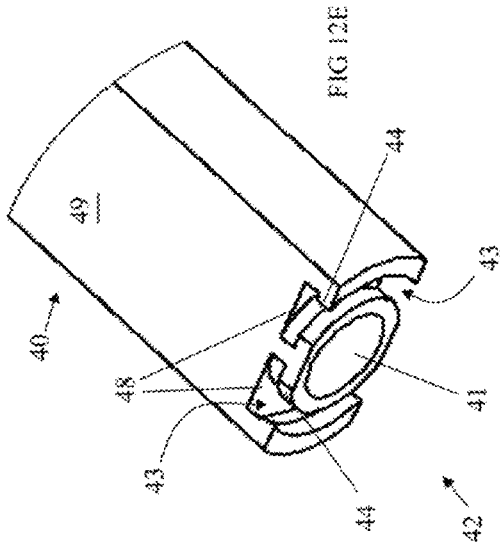
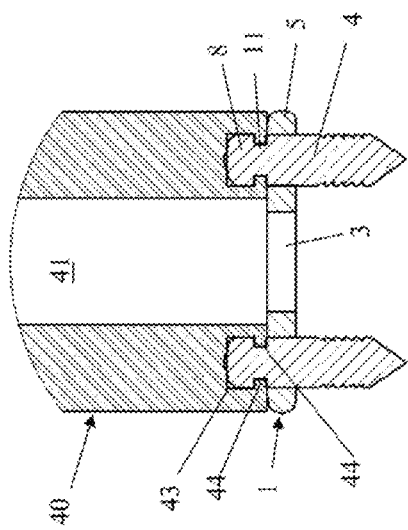
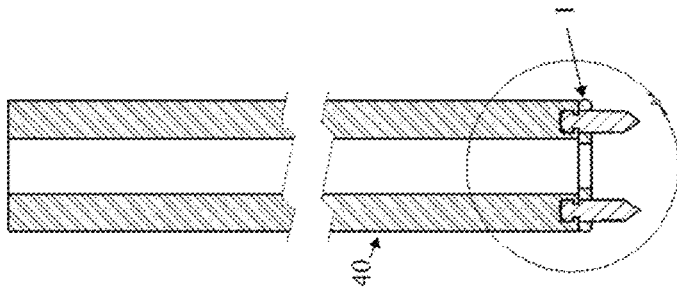
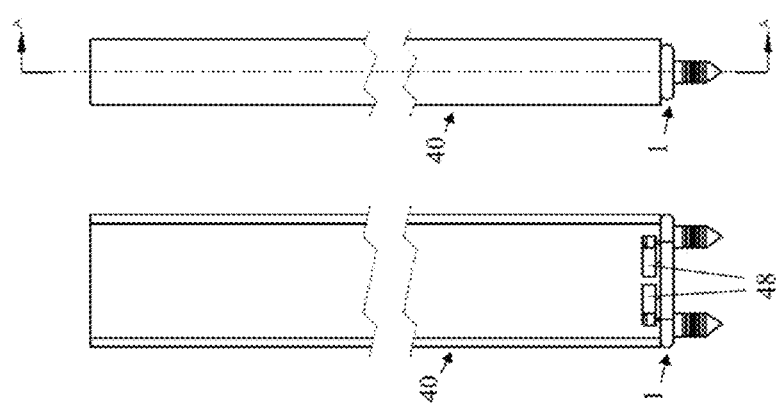

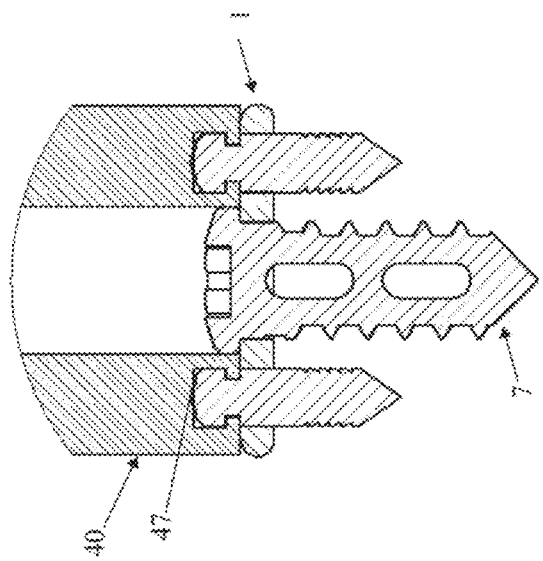
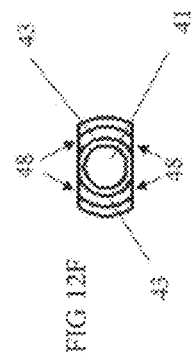
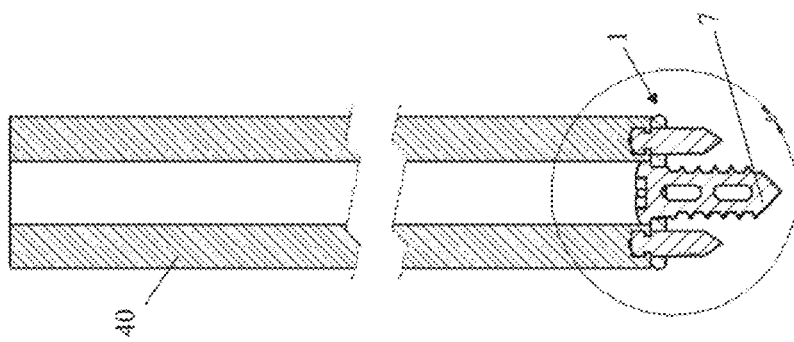
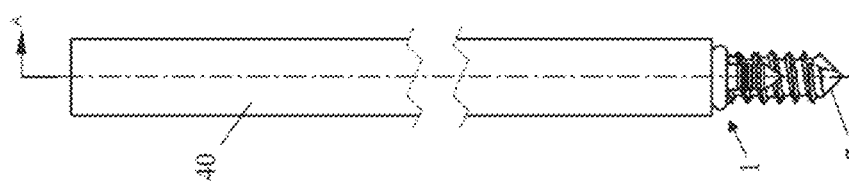
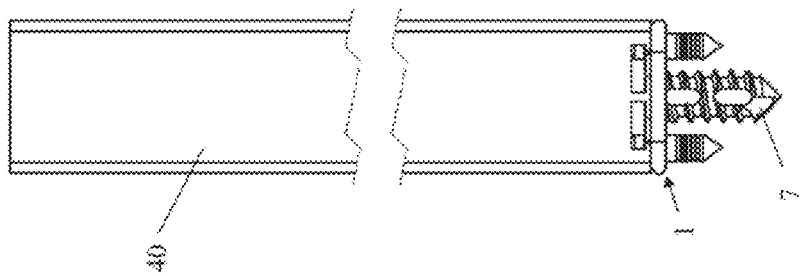

METHOD OF LATERAL FACET APPROACH, DECOMPRESSION AND FUSION USING SCREWS AND STAPLES AS WELL AS ARTHROPLASTY

CROSS-REFERENCE TO RELATED APPLICATIONS

The present application is a continuation-in-part of U.S. patent application Ser. No. 12/283,438 for a "Method Of Lateral Facet Approach, Decompression And Fusion Using Screws And Staples As Well As Arthroplasty" filed Sep. 11, 2008 now U.S. Pat. No. 8,894,651 from which priority is derived and which is incorporated herein by reference. U.S. patent application Ser. No. 12/283,438 derives priority from provisional application 60/993,233 filed on Sep. 11, 2007 which is further incorporated herein by reference

BACKGROUND OF THE INVENTION

1. Field of the Invention

The present invention relates to a method of approach to the lateral cervical facet for the purposes of spondylosyndesis or arthoplasty techniques as well as related devices.

2. Description of the Background

Human spinal degeneration is a natural result of aging and may lead to a medical condition known as spinal stenosis in which the spinal canal narrows and compresses the spinal cord and neural structures. Spinal stenosis is often accompanied or even caused by a herniated intervertebral disk. Patients suffering from the condition often experience significant pain and limited range of motion and mobility. Laminectomy is a surgical procedure for treating spinal stenosis in which one or both lamina are removed, often along with the spinous process, in order to relieve the pressure on the spinal cord and the related pain. Unfortunately, this procedure suffers from one major drawback, namely that it can compromise the stability of the spine, particularly when performed in the cervical region of the spine but also in the lumbar and thoracic regions as well.

Cervical facet fusion is a procedure in which the facet joints between two or more vertebra are joined together to stabilize the spine and eliminate motion which may contribute to spondylosis, or continued degeneration, and prevent progressive deformity. Cervical facet fusion is commonly performed in conjunction with laminectomy. The standard approach for decompressive laminectomy and/or facet fusion is the posterior approach which may be performed through variety of methods. The classic method involves passing wires through drill holes in the articular processes and binding two longitudinal struts of bone to the posterior columns of the articular processes. Another technique uses lateral mass screws that are connected via a metal rod. However, regardless of the method used, the posterior approach for posterolateral cervical facet fusion is time-consuming, results in resection of important connective tissue and musculature, involves moderate blood loss and often results in the patient suffering from shoulder pain for a significant period after surgery. Posterior approach patients also usually require inpatient hospital care for 2 to 3 days, require drains and experience high incidence of surgical site infection.

A variety of devices from different manufacturers have been developed for utilization in spinal surgeries such as facet fusion. Many of these devices are intended for fusion or fixation of the vertebra in the cervical region and elsewhere. These devices commonly consists of one or more plates and screws, pegs, or rods with fixating connectors that may be joined to the bone in order to stabilize the spine. Other devices take the form of a staple. Considerable effort has been expended on preventing the counter-rotation and withdrawal of screws as well as the ability of the devices to secure adjacent vertebra. Considerably less effort has been expended on making such devices less intrusive and quicker to implant (while still maintaining efficacy).

Although the noted spinal fixation devices as well as others have furthered technological development, none are done through lateral cervical approach and none provide a small profile of fixation or arthroplasty. It would thus be advantageous to provide a cervical staple, screw fusion fixation or arthroplasty for lateral cervical facet joint that: (1) allows for a more precise and a much smaller profile of fixation than prior art devices, (2) imposes less blood loss, (3) minimizes surgical time (4) avoids traction on the esophagus and trachea as in the anterior approach, (5) is minimally invasive, (6) is lightweight, and (7) is inexpensive to manufacture and sell to provide for widespread use. It would further be advantageous to provide the tools necessary to perform such a procedure such as a staple delivery guide device that is accurate, precise, and quick to load and deploy.

A novel lateral approach is herein proposed for facet fixation and fusion or arthroplasty that avoids many of the drawbacks of the known approaches. The lateral approach is done through a minimally invasive method, offers direct access to the facet joint, provides secure stabilization, and permits early mobilization of the patient.

SUMMARY OF THE INVENTION

Accordingly, it is an object of the invention to provide a surgical screw including holes or perforations along the threaded body and central shaft of the screw to allow bone growth there through and facilitate fusion of a facet joint.

Another object is to provide a quick solid fixation staple and method to add stability to the spine in patients who have not had prior surgical stabilization of the spine or for patients who have previously undergone surgical fusion anteriorly. It is a further object to secure overlay graft material on the vertebral surface to promote long term fixation.

An additional object is to provide a cervical staple and a surgical screw that are inexpensive to manufacture and sell to provide for widespread use.

Yet another object is to provide a method of lateral cervical facet fusion, which is a minimally invasive surgical method and that reduces attending staff requirements and operative time.

Yet another object of the present invention is to provide a staple placement guide and method of use that retains, places and releases a vertebral staple with certainty and precision.

These and other objects are accomplished by a lateral approach to facet fusion which involves less surgical time, reduced blood loss and discomfort for the patient as compared to the posterior approach. The lateral approach to facet fusion involves identifying the lateral mass and then introducing any of the fixation methods known or described herein laterally at one or more facets through the use of Kirschner wire (K-wire) and a hollow staple guide delivery device to deliver a surgical bone staple across the lateral facet joint where fixation is required. Where fusion is desired, a bone screw having lateral perforations of the shank is inserted at the joint to promote fusion. The staple and screw may be used in conjunction with one another or individually.

BRIEF DESCRIPTION OF THE DRAWINGS

Other objects, features, and advantages of the present invention will become more apparent from the following detailed description of the preferred embodiment and certain modifications thereof, in which:

FIG. 12A is a front view of a staple guide loaded with a staple according to the present invention.

FIG. 12B is a side view of a staple guide loaded with a staple according to the present invention.

FIG. 12C is section view of a staple guide loaded with a staple according to the present invention along A-A of FIG. 12B.

FIG. 12D is partial section view of a staple guide loaded with a staple according to the present invention at Detail B of FIG. 12C.

FIG. 12E partial perspective view of a distal end of a staple guide according to the present invention.

FIG. 12F is bottom view a staple guide according to the present invention.

FIG. 13A is a front view of a staple guide loaded with a staple and screw according to the present invention.

FIG. 13B is a side view of a staple guide loaded with a staple and screw according to the present invention.

FIG. 13C is section view of a staple guide loaded with a staple and screw according to the present invention along A-A of FIG. 13B.

FIG. 13D is partial section view of a staple guide loaded with a staple according to the present invention at Detail B of FIG. 13C.

DETAILED DESCRIPTION OF THE PREFERRED EMBODIMENTS

The present invention provides for a minimally invasive surgical implantation method and apparatus for cervical spine implants that preserves the structure and to a limited degree the function of the spine. In addition to stabilization by instrumentation, embodiments of the invention provide for introduction of graft material at or near the facet joint for promotion of joint fusion.

Two facet joints are formed between each pair of adjacent vertebrae of the human spine. Each vertebra has two superior articulating facets and two inferior articulating facets, with each superior facet of a lower vertebra meeting and aligning with an inferior facet of an upper vertebra to form one facet joint on each side of the spine. In the cervical spine, the upward inclination of the superior articular surfaces of the facet joints allows for considerable flexion and extension, as well as for lateral mobility. Each facet joint is covered by a dense, elastic articular capsule that is lined by a synovial membrane that secretes synovial fluid to lubricate the facet joint. The exterior of the joint capsule is surrounded by a capsular ligament that must be cut or displaced as part of some embodiments of the presently disclosed method for fusing the facet joints.

Figure 1:
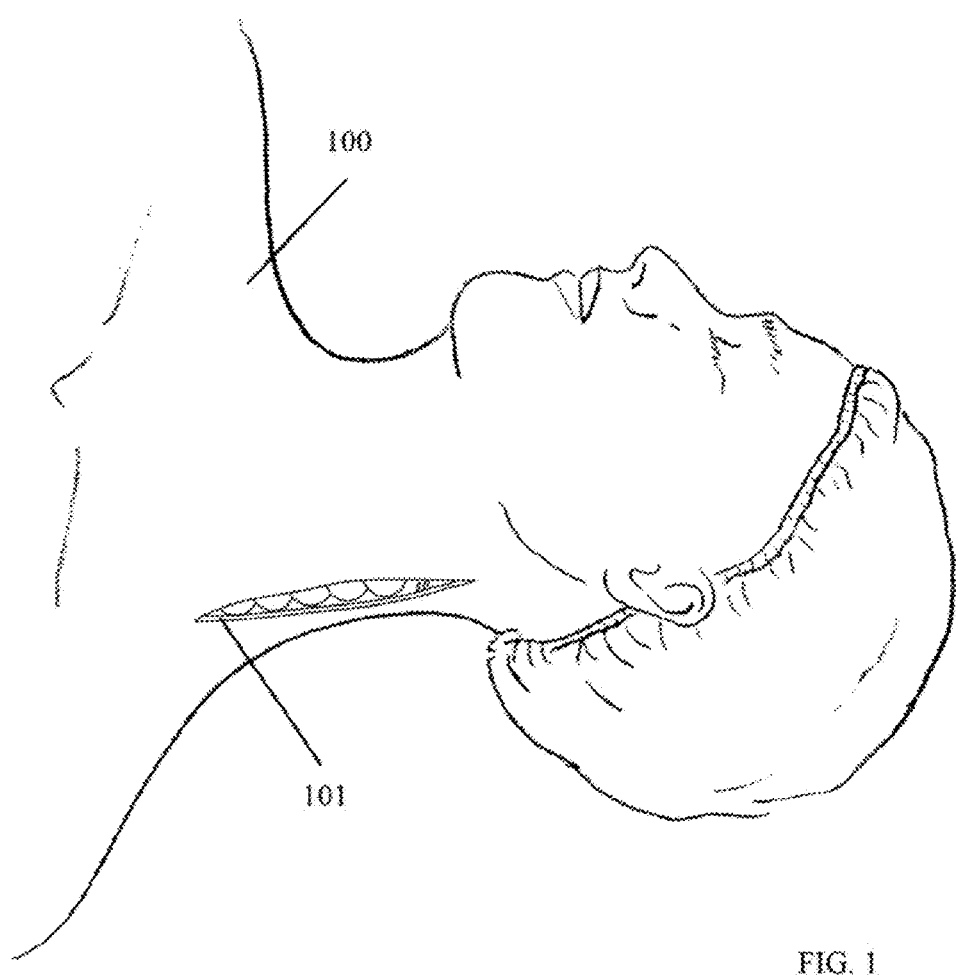
FIG. 1 is a perspective view of a patient indicating the dermal incision for lateral approach.
Figure 2:
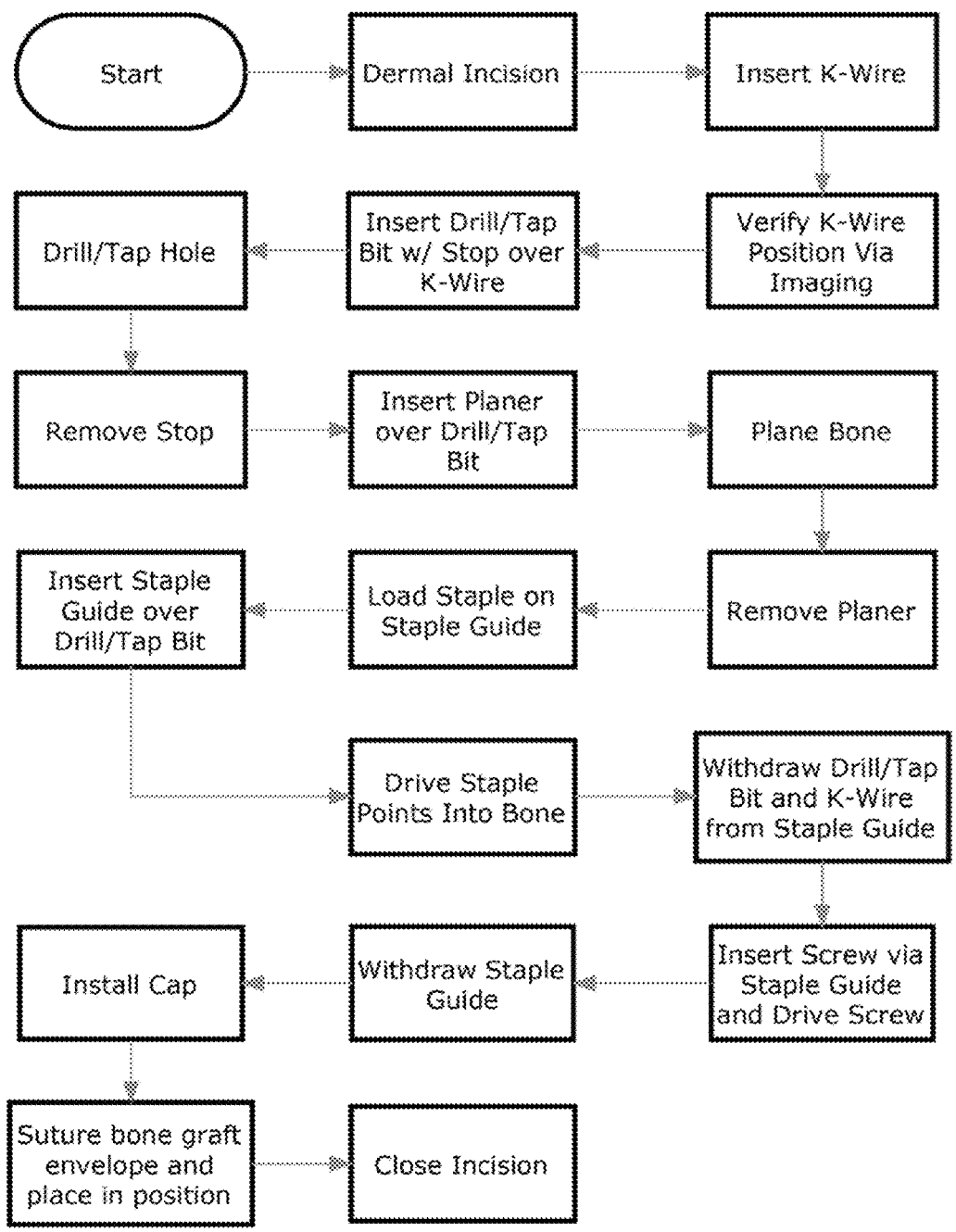
FIG. 2 is a diagram of the steps for lateral facet approach and fusion using screws and staples according to the present invention.
Figure 7:
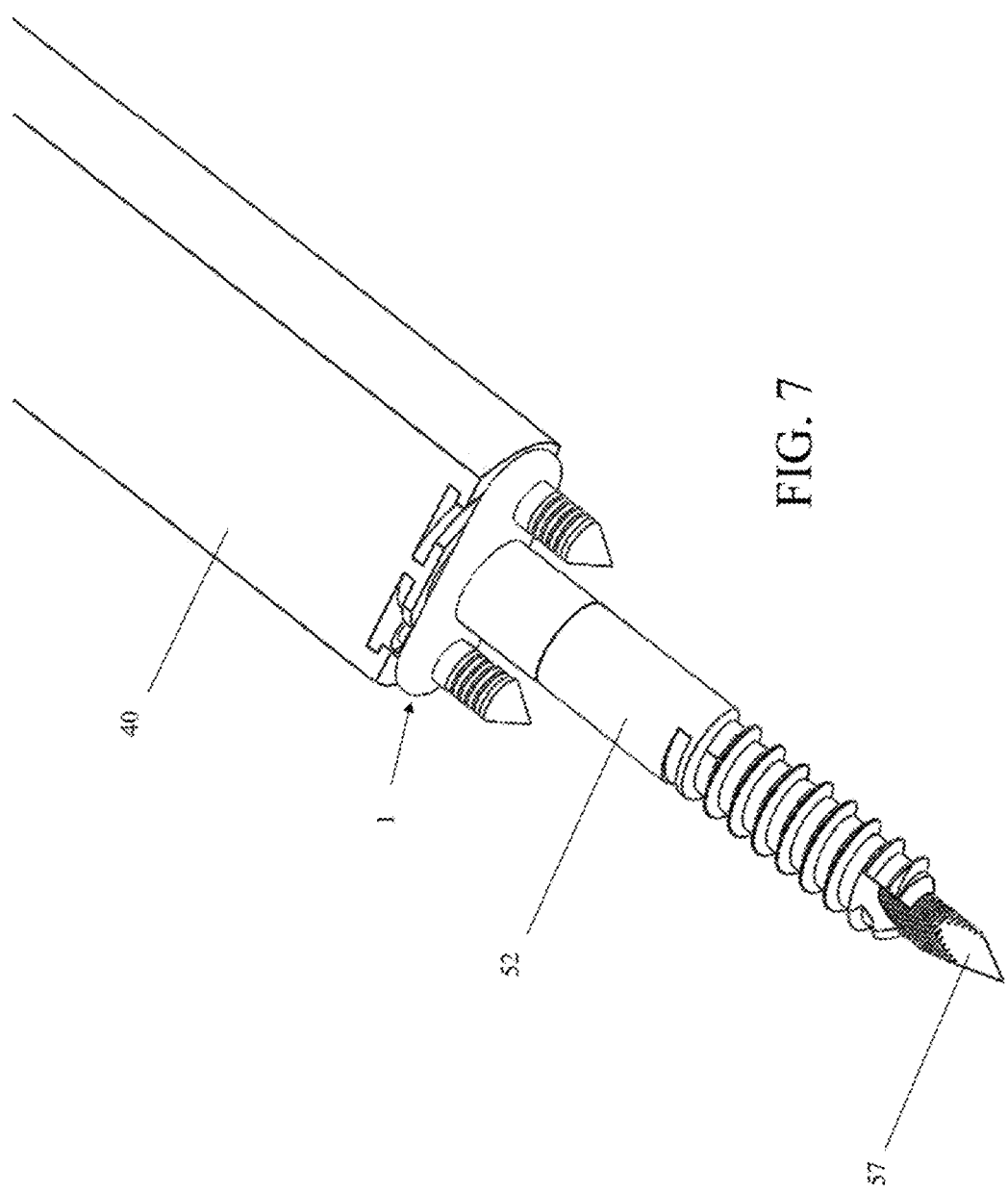
FIG. 7 is a partial perspective view of the loaded staple guide advanced over the cannulated drill bit and K-wire.

FIG. 1 depicts the neck region of a patient 100 indicating the position of the dermal incision 101 for lateral approach. With reference to FIGS. 2 and 7, after initial incision a Kirschner wire or K-wire 57 is inserted past the medial or posterior scalenes or trapezius muscle, depending on the particular cervical vertebra to be fused, to reach the intended facet joint. The K-wire 57 is inserted into the facet joint within medial plane of the joint in which the articular cartilage typically resides. The orientation of the medial plane of the joint will vary depending on the vertebral position in along the spine. The K-wire 57 may be smooth walled or, preferably threaded as depicted in FIG. 7 to provide greater holding power within the join. A trocar end is also preferred. The K-wire is used to facilitate alignment of instruments at the facet without impingement on the surrounding structures. The spinal accessory nerve is the only critical structure in the area that should be avoided. Injury to the nerve will cause paralysis of the scapula muscles. Particular care should be taken where threaded K-wire is utilized in order to avoid damage to the nerve. The location of the K-wire in relation to the facet joint is monitored and verified by medical imaging techniques such as X-ray imaging. Most desirably surgical direct semiconductor detection is used to provide real time monitoring.

Once the K-wire 57 is in position a cannulated drill bit 52 with drill guide and stop is inserted over the wire and advanced to the bone surface. In a preferred embodiment the cannulated drill bit 52 includes an integral tap portion to simultaneously tap the interior surface of the pilot hole as the drill is advanced. In an alternate embodiment a separate cannulated tap may be advanced over the K-wire to tap the pilot hole after removal of the cannulated drill bit. A surgical drill is used to drive the bit while the drill guide and stop limits the depth of the pilot hole to slightly less than the ultimate length of the screw (from the bottom of the head) (as described below) and in any event less than the opposing faces of the facet joint so as not to penetrate entirely through the joint. The bit diameter is preferably 1 mm smaller than the minor diameter of the bone screw 7 (FIG. 3) such that where, for example, 4.5 mm and 5.5 mm diameter bone screws are contemplated for use at varying points along the spinal column, 3.5 mm and 4.5 mm bit diameters would be utilized, respectively.

After drilling of the pilot hole the drill guide and stop are removed and a Calcar type bone planer is advanced over the cannulated drill bit 52 which preferably remains in place to stabilize the joint and maintain a centered position in the pilot hole. In an alternate embodiment the bit may be removed and the planer advanced over the K-wire only or advanced over the K-Wire prior to utilization of the bit to prepare the pilot hole. The planer is advanced to the bone surface and used to prepare a flat area in the cortical layer for seating of the staple as described below. The diameter of the plane should be approximately equal to or slightly greater than the length of the staple bridge 5 (see FIG. 4), also as described below. The planer is removed. If not already completed simultaneous with the drilling step, a cannulated tap may be advanced over the K-wire to tap the hole (after removing the cannulated drill bit) and thereafter remain in place on the K-wire as a centered guide.

Figure 4:
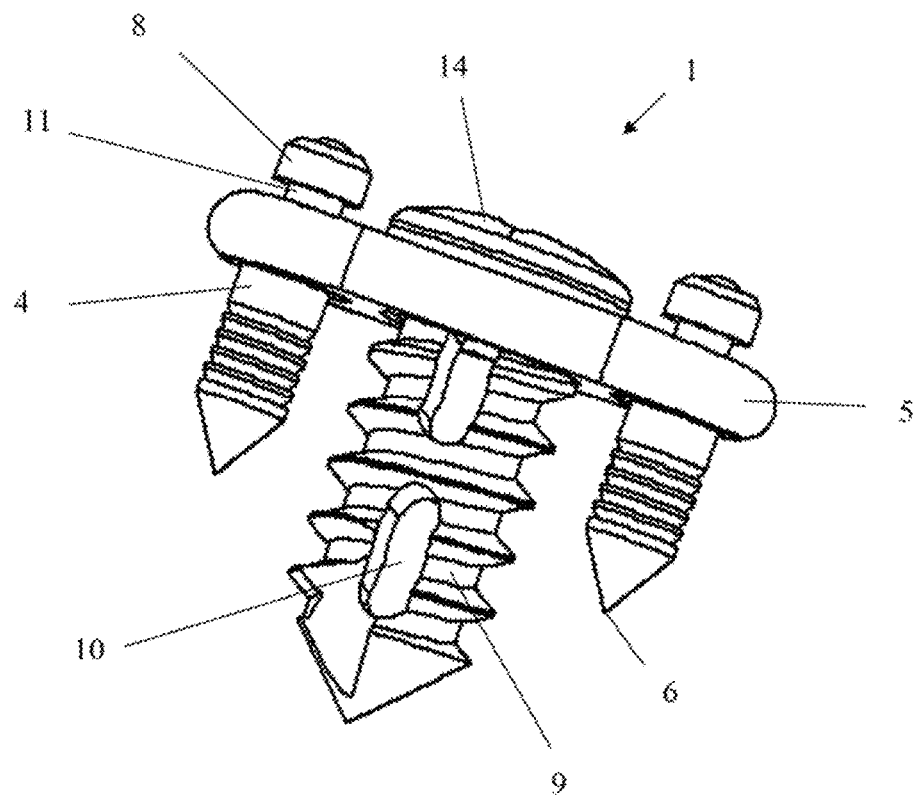
FIG. 4 is a side perspective view of the screw in conjunction with the staple.
Figure 5:
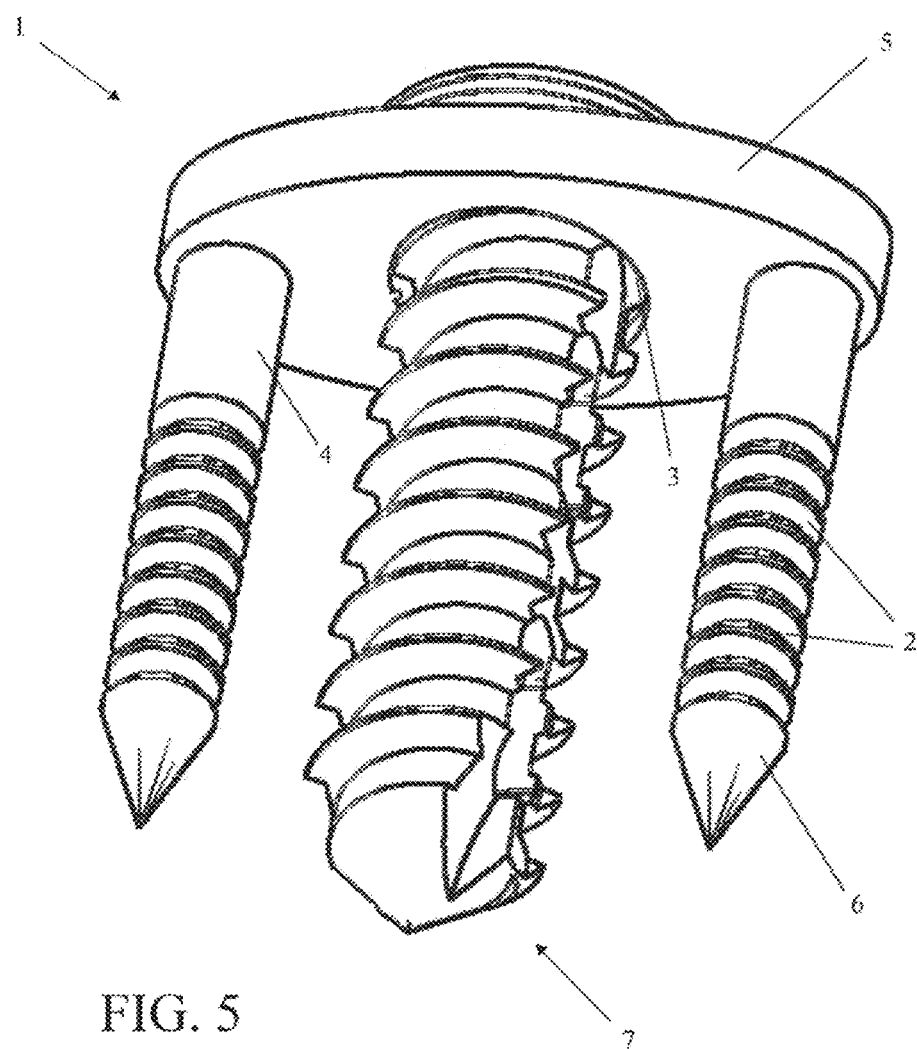
FIG. 5 is a bottom perspective view of the screw in conjunction with the staple.

A bone staple 1, as depicted in FIGS. 4 and 5, is inserted over the facet joint via a staple guide 40 (FIG. 6). The bone staple 1 includes at least first and second legs 4 joined by and extending from the lower surface of a bridge 5 that joins them at or near their proximal end. The legs each terminate at their distal end in a bevel or point 6 that is able to penetrate cortical bone. In the depicted embodiment the legs 4 extend through and above the upper surface of the bridge 5 to form pins 11 terminating in annularly enlarged heads 8. It should be noted that while legs 4 are depicted as contiguous members extending both above and below the bridge 5 (from tip to head), the legs need not be so limited. That is to say, the pins 11 extending from the upper surface of the bridge may be offset from the legs 4 extending downward from the lower surface of the bridge. Further, the pins 11 may be entirely separate members positioned on the upper surface of the bridge without regard to the position of the legs on the lower surface.

A hole or aperture 3 is provided from the upper surface of the bridge 5 to the lower surface. The relative position of the aperture with respect to the pins 11 or edges of the bridge 5 (depending on the embodiment) is critical to proper loading and deployment of the staple in and by the staple guide 40 as described below. The position of the legs 4 with respect to the aperture is less critical and, in as much as the staple is intended to span the facet joint, it is sufficient that at least one leg be provided on either side of the aperture so as to penetrate both adjacent vertebra. Preferably, as seen in FIG. 4, both legs are defined by a plurality of annular or outwardly oriented notches 2 formed with beveled walls defining a serrated outer surface that resist withdrawal from the bone once inserted. Legs 4 are preferably from 4 mm to 8 mm in length, more preferably 5 mm 7 mm, and from 2 mm to 4 mm in diameter, more preferably 2 mm.

Pins 11 extend to and terminate in enlarged heads 8 which are preferably flat. The heads 8 may be provided with a slightly conical upper surface or, preferably, a small protrusion (as depicted) to serve as a standoff from the surface of the staple guide and detent when loaded therein as described below. Alternately, the heads 8 may be with a ball, dome or other form for cooperative engagement with the staple guide 40.

The bridge 5 is a planar member that has its maximum length along a major axis that is greater than or equal to its length along a perpendicular minor axis. In a preferred embodiment pins 11 are symmetrically positioned along the major axis on either side of an aperture 3 that is also centered on the major axis. The aperture 3 extends from the upper surface of the bridge 5 to its lower surface and may be provided at its perimeter with a recess for countersinking the head 14 of the bone screw 7 (described below) into the bridge 5 for greater resistance to lateral movement of the staple 1. Alternately, the upper surface of the bridge 5 may be flat to engage the underside of the head 14 as depicted.

Figure 8:
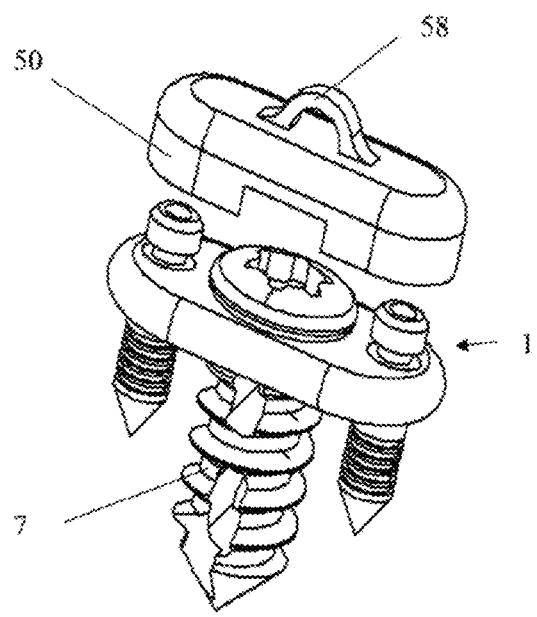
FIG. 8 is a perspective view of the staple with the screw installed and the cap exploded.

In the preferred embodiment the legs 4, like the pins 11, are symmetrically positioned along the major axis on either side of the aperture 3 but, as noted, it is not critical that this be so. The bridge 5 is preferably rectilinear in form having side edges parallel to the major axis and joined by rounded or arcuate ends, as depicted in FIG. 8. The bridge 5 may alternately be elliptical in shape (as depicted in FIG. 5), having length along its major axis equal to or greater than that along the minor axis, or any other planar form. The bridge 5 is preferably from 10 mm to 16 mm in length and pins 11 are preferably approximately 7 mm to 12 mm on-center and more preferably 9 mm on center. Legs 4, pins 11 and bridge 5 are preferably constructed of durable, surgically, implantable material such as titanium or stainless steel. Bridge 5 may alternately be constructed of PEEK and may be integrally formed or connected via known manufacturing techniques including welding, compression and mechanical integration.

With reference to FIGS. 6A-D and 12A-F, the staple guide 40 is a cannulated rod preferably approximately 100 mm in length characterized by a central longitudinal void 41 extending though its length to a distal end 42, the void 41 being preferably but not necessarily centered within the cross section of the guide. The distal tip 42 of the guide 40 is provided with a structure to selectively capture and release the heads 8 of the staple 1 by relative rotation of the staple and guide. In a preferred embodiment an annular channel 43 is provided in the distal end 42 of the guide 40 encircling a point of rotation. It is preferred that the point of rotation be the center of the guide 40 cross section and it is further preferred that the point of rotation be concentric with the longitudinal void 41. Those skilled in the art may observe that where the annular channel is not concentric about the longitudinal void, it will be sufficient that the aperture 3 be aligned with the longitudinal void when captured in the staple guide 40.

Figure 6A:
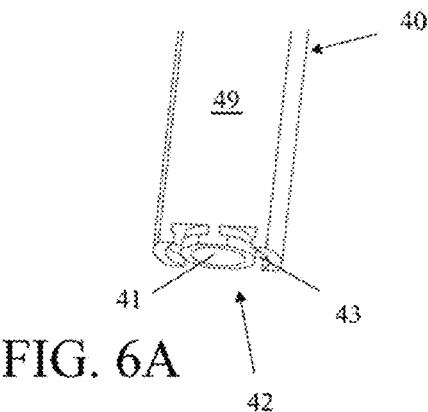
FIG. 6A is a partial perspective view of the distal end of the staple guide.
Figure 6B:
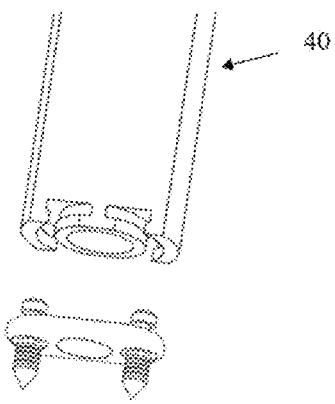
FIG. 6B is a partial perspective view of the distal end of the staple guide relative to the staple of the present invention.
Figure 6C:
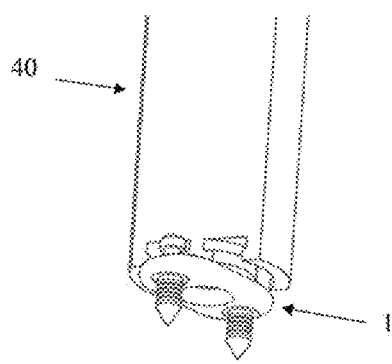
FIG. 6C is a partial perspective view the staple of the present invention being loaded onto the distal end of the staple guide before rotation.
Figure 6D:
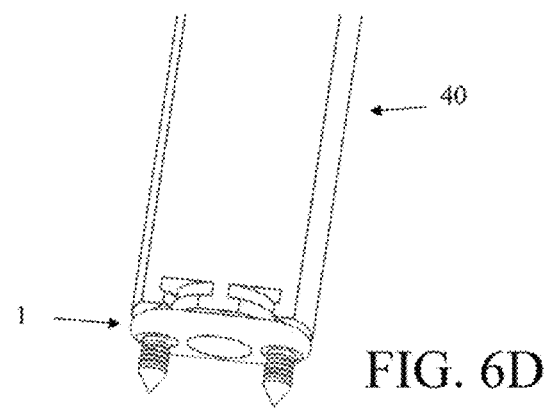
FIG. 6D is a partial perspective view the staple of the present invention fully loaded onto the distal end of the staple guide.

The inner and outer walls of the channel 43 are each provided with an annular protrusion 44 such that the channel 43 cross section has a necked form that will capture the enlarged heads 8 of the pins 11 of the staple 1. The size and spacing of heads 8 are chosen for cooperative engagement within the channel 43, as depicted in FIG. 6D or 12D. In order to be able to start the heads 8 into the channel 43 lateral openings 48 are provided by removing a segment of the channel 43 on opposing side of guide 40 and thereby creating flat sides 49 on the guide 40. The cord length of the opposing circular segments removed from the staple guide cross section are chosen to tangentially intersect the inner wall of the channel 43. To load the staple 1 into the guide 40 the major axis of the staple is oriented perpendicular to the flat sides 49 of the guide 40 (as in FIG. 6C) and the flat sides advanced and positioned between the heads 8 of staple. The staple can then be rotate 90 degrees (as in FIG. 6D so that the pins 11 and heads 8 enter the channel 43 via the lateral openings 48, the enlarged heads being engaged by the annular protrusions 44 to retain the staple in place until the rotation is reversed to release the pins and staple after implantation. A dimple 47 may be provided within the channel 43 to receive the small protrusion provided the top of head 8 to act as a detent securing the staple 1 in the guide. In this loaded position the aperture 3 of the staple is necessarily concentrically aligned with void 41 of the guide 40.

With reference to FIG. 7, the void 41 of the guide 40 is sized slide over the cannulated drill bit 52 which, as stated, remains in the pilot hole during portions of the procedure as a centering guide. In an alternate embodiment in which the bit has been removed and a separate tap has been used to prepare the inner surface of the pilot hole, the guide would be sized to slide over the tap which would remain in place to serve as a guide in lieu of the bit. The loaded staple guide 40 is positioned over the K-wire 57 and cannulated bit 52 and advanced to the bone surface such that the distal tips 6 of the legs 4 engage the surfaces of the vertebrae, one on either side of the facet joint. In this way the aperture 3 of the bridge 5 is necessarily aligned with the pilot hole in the joint which remains supported and aligned by the drill bit. The legs 4 of the staple 1 are then driven into the bones by force. Force may be applied by manually by the surgeon or by surgical bone hammer, slide hammer integral to the staple guide 40, or other known surgical technique. With the staple secured across the facet joint the K-wire and cannulated drill bit are removed from the pilot hole via the central void 41 of the staple guide 40 which remains in place and engaged to the staple 1. A bone screw 7 is delivered via the now vacant central void 41 of the staple guide 40, as depicted in FIGS. 7 and 13A-D, and rotationally driven through the aperture 3 of the staple bridge 5 into the pilot hole in the bone by a cooperative driving tool engaging screw head 14. The driving tool (not pictured) is advanced through the void 41 of the guide 40. After the staple 1 is secured in place by the screw 7 the staple guide 40 is rotated about is longitudinal axis to release the heads 8 of the pins 11 from the channel 43 via lateral openings 48, thus permitting the staple guide 40 to be removed.

In an alternate embodiment, the pins 11 and heads 8 of the staple 1 are omitted altogether as is the inner wall of the arcuate channel 43 at the distal end 42 of the guide 40. In such an embodiment staple is loaded into the guide by inserting the bridge 5 between the outer walls of the arcuate channel and rotating as described above such that the arcuate ends of the bridge are captured between the outer walls of the arcuate channel which are provided with an annular protrusion as described above.

In yet another alternate embodiment, the lateral openings 48 are omitted by failing to remove the opposing segments of the channel 43 in favor of distal openings. Distal openings are formed by omitting a portion of the lateral protrusions at opposing positioned around the arcuate channel such that the heads 8 of the pins 11 can be advanced into the channel from a distal position before being rotated into the channel and captured.

Figure 3:
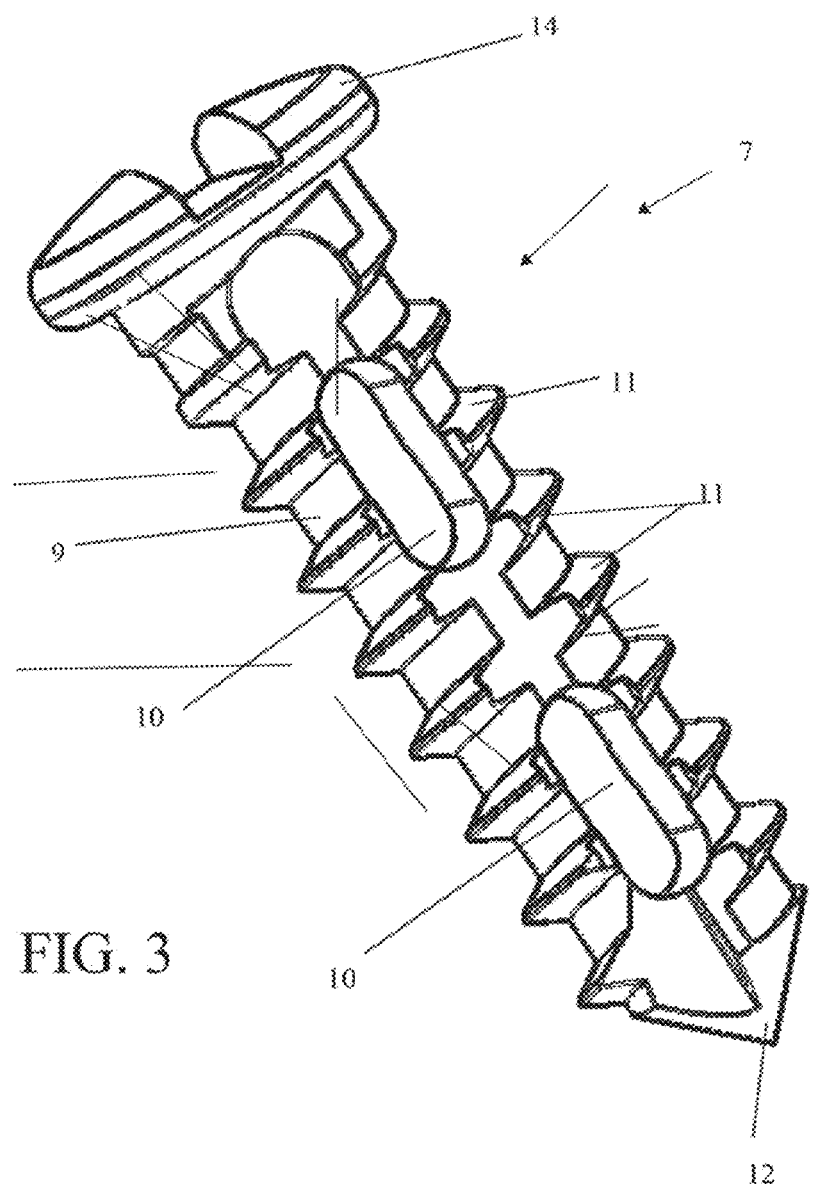
FIG. 3 is a front perspective view of the screw.

Bone screw 7 may be any known bone screw but is preferably a screw having a cylindrical, externally shank 9 topped at one end by a head 14 adapted to be engaged by a fastener-driving tool as depicted in FIGS. 3, 4 and 5. The shank 9 of the screw 7 may be hollow along some or all of its length and is further preferably provided with one or more perforations 10 positioned along the linear axis of the shank 9 and extending through the shank 9 perpendicular to its linear axis are provided to allow bone growth through the screw in order to fuse the joint into which it is driven and secure the screw in place. The distal tip of the screw may be blunt or may be tapered to a sharp point 12.

Figure 9:
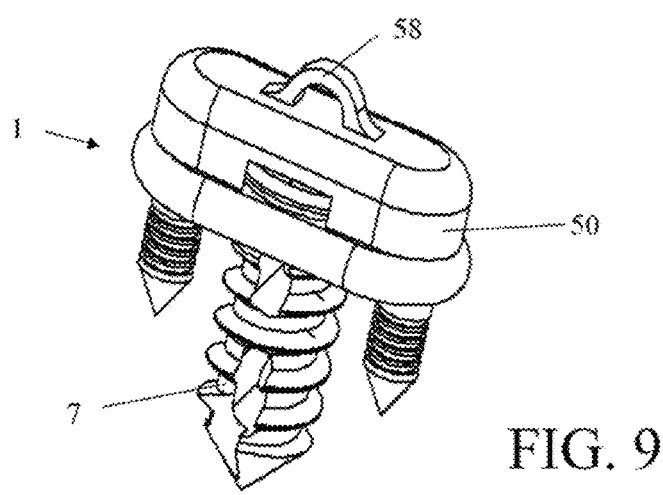
FIG. 9 is a perspective view of the staple with the screw installed and the cap in position.

With reference to FIGS. 8 and 9, after the staple 1 is secured in place in the facet joint by screw 7 a cap 50 is placed over the visible portions of the staple. The cap 50 is cooperatively formed to envelope the exposed surface of the bridge 5 and screw 7. The cap 50 is provided with resilient members on its inner surface which engage the heads 8 of the pins 11 by snap fit or friction fit so as to removeably secure the cap 50 in place over the staple 1. A loop 58 on the outer surface of the cap 50 is provided to which bone graft material may be secured. In a preferred embodiment an envelope 59 containing bone graft material may be sutured to the loop 58 and positioned between the transverse processes of the affected vertebrae or directly on the surface of the inferior vertebral lamina depending on the location of the site along the spine. The envelope is preferably made of woven polyethylene or polyester fabric and may contain allograft, autograft or synthetic graft material, with or without human osteogenic growth factors, such as bone morphogenetic proteins, transforming growth factor, and platelet-derived growth factor. Fusion at the transverse process or lamina by only graft serves to further secure and support stability of the facet joint. After the graft material is secured in position the incision is closed.

Figure 10:
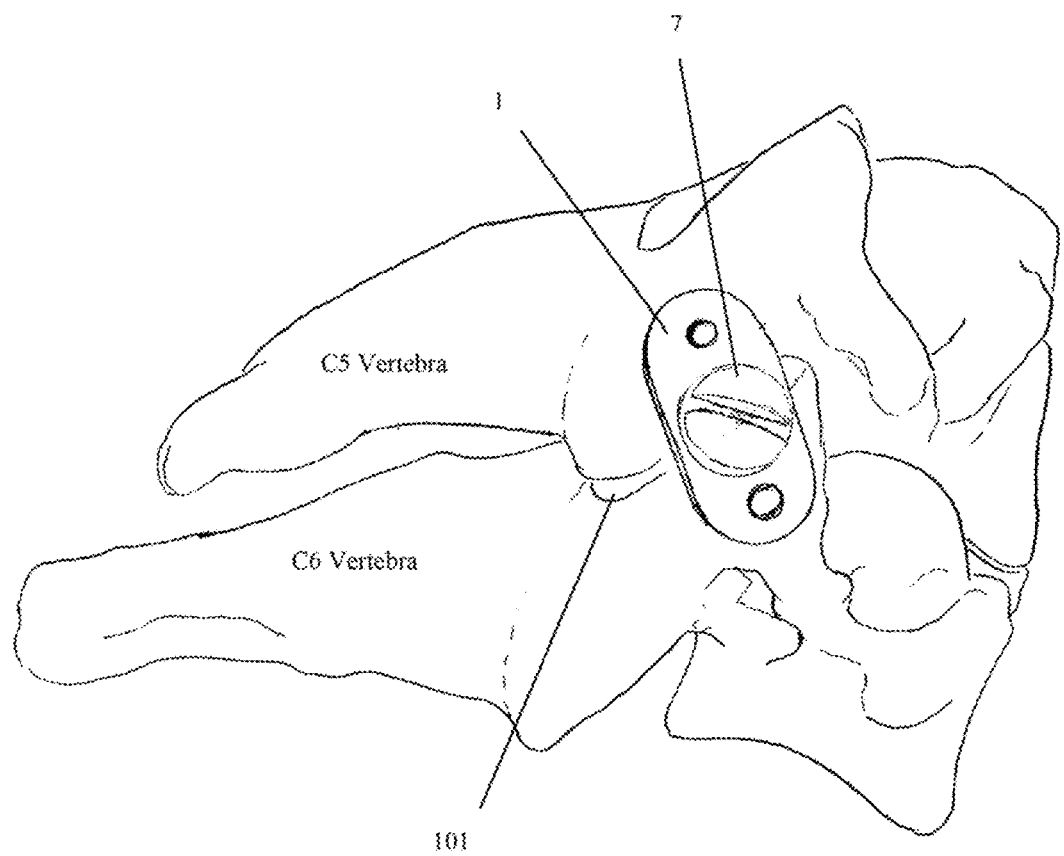
FIG. 10 is a perspective view of the screw and staple installed in the C5-C6 facet joint before the cap is in place.
Figure 11:
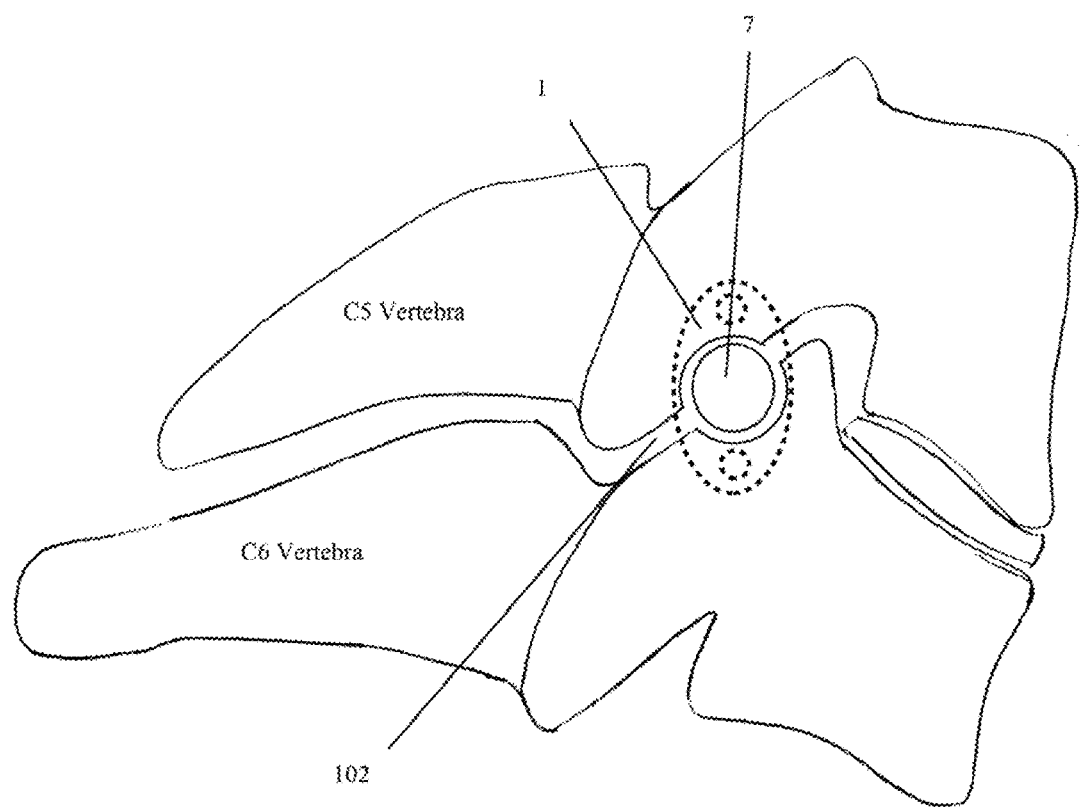
FIG. 11 is an abstracted section of the C5 and C6 vertebra showing the location of the screw and staple.

FIG. 10 depicts the location of bone screw 7 and staple 1 after implantation to stabilize the right C5-C6 facet joint 101. The cap 50 and bone envelope 59 are omitted for clarity. FIG. 10 is an abstraction of the C5-C6 vertebra indicating the position of the screw 7 and staple 1 in the facet joint 102. It should be noted that the C5-C6 facet joint here is referenced by way of illustration and the present method may be utilized at other cervical and non cervical joints.

The above-described lateral approach to facet fusion and related devices can be equally applied to other areas of the spine including the lumber and thoracic regions. Although the staple 1, screw 7 and cap 50 have particular utility for the lateral approach to facet fusion, one skilled in the art will understand that the present invention can be equally applicable to other approaches to facet fusion and to fusion or fixation of other skeletal structures.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

We claim:

1. A kit for performing vertebral facet fusion by lateral approach comprising, in combination:
   a drill bit having a first diameter;
   a bone staple, comprising,
      a bridge having an upper surface and a lower surface and a circular aperture extending from said upper surface to said lower surface, said aperture having second diameter that is larger than said first diameter and cooperatively selected therewith such that said bone staple can be advanced along said drill bit when said drill bit is received in said circular aperture;
      a pair of legs extending from said lower surface of said bridge, one of said legs positioned on either side of said aperture; and
      a pair of pins extending from said upper surface of said bridge and each terminating at a distal end in an annularly enlarged head, one of said pins positioned on each side of said aperture;
   a bone staple guide for implanting said bone staple into vertebral bone, comprising,
      a cannulated rod having a cylindrical axial void extending from a first opening at a distal end to a second opening at a proximal end for through-access to said bone, said axial void having a third diameter that is larger than said first diameter,
      an annular channel formed in said distal end and at least partially encircling said first opening, said annular channel bounded by an inner wall and an outer wall, said inner wall and outer wall each rimmed with an annular protrusion extending sidelong into said channel, and
      a plurality of openings into said annular channel;
   wherein said aperture of said bone staple is concentrically aligned with said axial void of said bone staple guide when said pins are received in said annular channel via said plurality of openings into said annular channel;
   whereby said bone staple guide may be coaxially advanced over said drill bit when said bone staple is captured on said distal end of said bone staple guide by said receipt of said pins in said annular channel;

said kit further comprising a bone screw having an annular head atop an externally-threaded body, said head having a maximum diameter less than said third diameter and greater than said second diameter, and said body having a diameter less than or equal to said first diameter;

whereby upon removal of said drill bit from said axial void of said staple guide, said bone screw can be advanced through said axial void and said body of said bone screw can be further advanced through said aperture of said bone staple to secure said bone staple to said vertebral bone.

2. The kit for performing vertebral facet fusion by lateral approach of claim 1 wherein said legs of said bone staple further comprise a plurality of serrations along at least a portion of a length thereof.

3. The kit for performing vertebral facet fusion by lateral approach of claim 2 wherein said serrations are annular with respect to each leg.

4. The kit for performing vertebral facet fusion by lateral approach of claim 1 wherein said legs of said bone staple each further comprise a pointed distal end for penetration of said bone.

5. The kit for performing vertebral facet fusion by lateral approach of claim 4 wherein said pointed distal end is a sharp beveled point.

6. The kit for performing vertebral facet fusion by lateral approach of claim 1 further comprising a cap substantially covering said bridge and secured in place by snap fit with said pins, said cap further comprising a loop to which bone graft material may be secured.

7. The kit for performing vertebral facet fusion by lateral approach of claim 1 wherein said cannulated rod comprises a surface extending from said proximal end to said distal end and wherein said plurality of openings into said annular channel of said staple guide are lateral openings formed through said surface and cooperatively sized to receive said enlarged heads of said pins of said bone staple.

8. The kit for performing vertebral facet fusion by lateral approach of claim 1 wherein
said plurality of openings into said annular channel of said staple guide are distal openings formed through annular protrusions of said inner and outer walls of said channel, said distal openings cooperatively sized to receive said enlarged heads of said pins of said bone staple.

9. The kit for performing vertebral facet fusion by lateral approach of claim 1 wherein said inner wall defines said first opening of the axial void at the distal end of said cannulated rod.

10. The kit for performing vertebral facet fusion by lateral approach of claim 1 wherein said axial void is concentric with said channel.

11. The kit for performing vertebral facet fusion by lateral approach of claim 1 wherein said inner wall and said outer wall of said channel are joined by a channel bottom, said channel bottom further comprising a pair of recesses formed therein cooperatively positioned so as to retain therein said pins extending from said upper surface of said bridge of said bone staple.

12. The kit for performing vertebral facet fusion by lateral approach of claim 11 wherein said pins extending from said upper surface of said bridge of said bone staple further each comprise a protrusion extending from said annularly enlarged head thereof for cooperative engagement in said pair of recesses.

* * * * *